US010767308B2

(12) United States Patent
Jansen et al.

(10) Patent No.: US 10,767,308 B2
(45) Date of Patent: Sep. 8, 2020

(54) METHODS FOR SEPARATING AND REFINING LIGNIN FROM BLACK LIQUOR AND COMPOSITIONS THEREOF

(71) Applicant: VIRDIA, INC., Raceland, LA (US)

(72) Inventors: Robert Jansen, Collinsville, IL (US); James Alan Lawson, Ellsworth, ME (US); Noa Lapidot, Mevaseret Zion (IL)

(73) Assignee: VIRDIA, INC., Raceland, LA (US)

( * ) Notice: Subject to any disclaimer, the term of this patent is extended or adjusted under 35 U.S.C. 154(b) by 0 days.

(21) Appl. No.: 15/319,935

(22) PCT Filed: Jul. 7, 2015

(86) PCT No.: PCT/US2015/039438
§ 371 (c)(1),
(2) Date: Dec. 19, 2016

(87) PCT Pub. No.: WO2016/007550
PCT Pub. Date: Jan. 14, 2016

(65) Prior Publication Data
US 2017/0130398 A1 May 11, 2017

Related U.S. Application Data

(60) Provisional application No. 62/022,644, filed on Jul. 9, 2014.

(51) Int. Cl.
*D21C 11/00* (2006.01)
*C07G 1/00* (2011.01)
(Continued)

(52) U.S. Cl.
CPC ............ *D21C 11/0007* (2013.01); *C07G 1/00* (2013.01); *C08H 6/00* (2013.01); *C12P 5/023* (2013.01);
(Continued)

(58) Field of Classification Search
CPC . D21C 11/0007; D21C 11/0085; C12P 5/023; C08H 6/00; C07G 1/00; Y02E 50/343; Y02P 20/582
(Continued)

(56) References Cited

U.S. PATENT DOCUMENTS 1,888,025 A 11/1932 Bent
2,037,001 A 4/1936 Aronovsky
(Continued)

FOREIGN PATENT DOCUMENTS

CA 2812685 A1 3/2012
CN 101143881 A 3/2008
(Continued)

OTHER PUBLICATIONS

EP15819321.9 Extended Search Report dated Dec. 14, 2017.
(Continued)

*Primary Examiner* — Fred Prince
(74) *Attorney, Agent, or Firm* — Wilson Sonsini Goodrich & Rosati

(57) ABSTRACT

The invention relates methods and processes for the separation and refining of lignin from spent cooking liquor, called black liquor, present in industrial chemical plants, and compositions thereof. A process is provided for separating black liquor into at least two, three, or four streams selected from: (i) a gaseous stream comprising volatile sulfur compounds; (ii) a lignin-comprising stream produced by extracting lignin into a limited solubility solvent S1; (iii) a salt stream, comprising solid sodium and sulfate salts; and (iv) a salt-depleted and lignin-depleted aqueous stream comprising hydrocarbons.

24 Claims, 4 Drawing Sheets

(51) Int. Cl.
*C12P 5/02* (2006.01)
*C08H 7/00* (2011.01)

(52) U.S. Cl.
CPC ......... *D21C 11/0085* (2013.01); *Y02E 50/343* (2013.01); *Y02P 20/582* (2015.11)

(58) Field of Classification Search
USPC ............ 210/603, 723; 106/273.1; 423/273.1, 423/445 R, 447.1; 44/436; 507/106; 521/155; 523/456; 530/500, 507; 554/1, 554/213; 560/1; 562/400; 568/303, 449, 568/700, 799; 585/469, 639, 733
See application file for complete search history.

(56) References Cited

U.S. PATENT DOCUMENTS

| | | |
|---|---|---|
| 2,042,705 A | 6/1936 | Henry et al. |
| 2,380,448 A | 7/1945 | Katzen |
| 2,669,592 A | 2/1954 | MacGregor et al. |
| 2,772,965 A | 12/1956 | Gray et al. |
| 3,461,082 A | 8/1969 | Otani et al. |
| 3,808,192 A | 4/1974 | Dimitri M |
| 4,111,928 A | 9/1978 | Holsopple et al. |
| 4,237,110 A | 12/1980 | Forster et al. |
| 4,277,626 A | 7/1981 | Forss et al. |
| 4,470,851 A | 9/1984 | Paszner et al. |
| 4,520,105 A | 5/1985 | Sinner et al. |
| 4,740,591 A | 4/1988 | Dilling et al. |
| 4,797,457 A | 1/1989 | Guiver et al. |
| 4,925,923 A | 5/1990 | Yalpani et al. |
| 4,946,946 A | 8/1990 | Fields et al. |
| 4,966,650 A | 10/1990 | Delong et al. |
| 5,177,169 A | 1/1993 | Schroeder |
| 5,730,837 A | 3/1998 | Black et al. |
| 5,811,527 A | 9/1998 | Ishitoku et al. |
| 5,865,948 A | 2/1999 | Lora et al. |
| 5,968,417 A | 10/1999 | Viswanathan |
| 6,022,419 A | 2/2000 | Torget et al. |
| 6,620,292 B2 | 9/2003 | Wingerson |
| 7,465,791 B1 | 12/2008 | Hallberg et al. |
| 7,649,086 B2 | 1/2010 | Belanger et al. |
| 7,678,358 B2 | 3/2010 | Eckert et al. |
| 7,699,958 B2 | 4/2010 | Griffith et al. |
| 7,794,824 B2 | 9/2010 | Eckert et al. |
| 7,842,162 B1 | 11/2010 | Lvov et al. |
| 9,139,681 B2 | 9/2015 | Fitchett et al. |
| 9,683,005 B2 * | 6/2017 | Jansen ............ C07G 1/00 |
| 9,783,861 B2 | 10/2017 | Jansen et al. |
| 9,988,412 B2 | 6/2018 | Jansen et al. |
| 10,138,332 B2 | 11/2018 | Jansen et al. |
| 2002/0065400 A1 | 5/2002 | Raskin et al. |
| 2003/0156970 A1 | 8/2003 | Oberkofler et al. |
| 2003/0221804 A1 | 12/2003 | Lightner |
| 2004/0060673 A1 | 4/2004 | Phillips et al. |
| 2004/0101459 A1 | 5/2004 | Schur |
| 2004/0108085 A1 | 6/2004 | Kettenbach et al. |
| 2004/0244925 A1 | 12/2004 | Tarasenko |
| 2007/0160926 A1 | 7/2007 | Ayaki et al. |
| 2008/0032344 A1 | 2/2008 | Fallavollita |
| 2008/0057555 A1 | 3/2008 | Nguyen |
| 2008/0202504 A1 | 8/2008 | Hilst |
| 2008/0317661 A1 | 12/2008 | Eckert et al. |
| 2008/0318043 A1 | 12/2008 | Eckert et al. |
| 2009/0062516 A1 | 3/2009 | Belanger et al. |
| 2009/0069550 A1 | 3/2009 | Belanger et al. |
| 2009/0176286 A1 | 7/2009 | O'Connor et al. |
| 2009/0229599 A1 | 9/2009 | Zhang et al. |
| 2010/0136642 A1 | 6/2010 | Belanger et al. |
| 2010/0159515 A1 | 6/2010 | Cirakovic |
| 2010/0159518 A1 | 6/2010 | Diner et al. |
| 2010/0159519 A1 | 6/2010 | Diner et al. |
| 2010/0269990 A1 | 10/2010 | Dottori et al. |
| 2010/0279361 A1 | 11/2010 | South et al. |
| 2010/0279372 A1 | 11/2010 | Cho et al. |
| 2010/0305241 A1 | 12/2010 | Balakshin et al. |
| 2011/0073805 A1 | 3/2011 | Dibble et al. |
| 2011/0274612 A1 | 11/2011 | Wohlmann et al. |
| 2011/0294991 A1 | 12/2011 | Lake et al. |
| 2011/0297340 A1 * | 12/2011 | Kouisni ............ D21C 11/0007 162/16 |
| 2012/0058526 A1 | 3/2012 | Jansen et al. |
| 2012/0116063 A1 | 5/2012 | Jansen et al. |
| 2012/0167874 A1 | 7/2012 | Jansen et al. |
| 2012/0226029 A1 | 9/2012 | Dodd |
| 2012/0289692 A1 | 11/2012 | Gray et al. |
| 2013/0172540 A1 | 7/2013 | Simard et al. |
| 2013/0183227 A1 | 7/2013 | Wohlmann et al. |
| 2013/0255216 A1 | 10/2013 | Argyropoulos et al. |
| 2014/0054506 A1 * | 2/2014 | Melin ................ D21C 11/0057 252/373 |
| 2014/0171379 A1 | 6/2014 | Jansen et al. |
| 2014/0227161 A1 | 8/2014 | Manesh et al. |
| 2014/0242867 A1 | 8/2014 | Jansen et al. |
| 2015/0141628 A1 | 5/2015 | Jansen et al. |
| 2016/0102113 A1 | 4/2016 | Jansen et al. |
| 2016/0130408 A1 | 5/2016 | Jansen et al. |
| 2017/0313826 A1 | 11/2017 | Jansen et al. |
| 2017/0349958 A1 | 12/2017 | Jansen et al. |

FOREIGN PATENT DOCUMENTS

| | | |
|---|---|---|
| CN | 101977664 A | 2/2011 |
| CN | 102027021 A | 4/2011 |
| CN | 102361914 A | 2/2012 |
| EP | 0211558 A2 | 2/1987 |
| EP | 0224721 A1 | 6/1987 |
| EP | 0224721 B1 | 6/1991 |
| EP | 0446556 B1 | 8/1995 |
| EP | 1272433 B1 | 1/2004 |
| GB | 1525508 A | 9/1978 |
| JP | 48-024003 | 3/1973 |
| JP | 51-097603 | 8/1976 |
| JP | S59204997 A | 11/1984 |
| JP | 62-110994 | 5/1987 |
| JP | 01-306618 A | 12/1989 |
| JP | 2011256380 A | 12/2011 |
| JP | 2012236811 A | 12/2012 |
| JP | 2013035885 A | 2/2013 |
| JP | 2013035886 A | 2/2013 |
| JP | 2016512285 A | 4/2016 |
| KR | 20130117776 A | 10/2013 |
| WO | WO-9641052 A1 | 12/1996 |
| WO | WO-0132715 A1 | 5/2001 |
| WO | WO-0202826 A1 | 1/2002 |
| WO | WO-2006086861 A2 | 8/2006 |
| WO | WO-2006086861 A3 | 10/2006 |
| WO | WO-2007019505 A2 | 2/2007 |
| WO | WO-2007019505 A3 | 6/2007 |
| WO | WO-2008079072 A1 | 7/2008 |
| WO | WO-2008144903 A1 | 12/2008 |
| WO | WO-2009002785 A1 | 12/2008 |
| WO | WO-2009021733 A2 | 2/2009 |
| WO | WO-2009028969 A1 | 3/2009 |
| WO | WO-2009021733 A3 | 6/2009 |
| WO | WO-2009068711 A1 | 6/2009 |
| WO | WO-2009104995 A1 | 8/2009 |
| WO | WO-2010043424 A1 | 4/2010 |
| WO | WO-2010045576 A2 | 4/2010 |
| WO | WO-2010060183 A1 | 6/2010 |
| WO | WO-2010045576 A3 | 7/2010 |
| WO | WO-2010081231 A1 | 7/2010 |
| WO | WO-2010146331 A2 | 12/2010 |
| WO | WO-2011007369 A1 | 1/2011 |
| WO | WO-2011037967 A2 | 3/2011 |
| WO | WO-2011057413 A1 | 5/2011 |
| WO | WO-2011097721 A1 | 8/2011 |
| WO | WO-2011151823 A1 | 12/2011 |
| WO | WO-2012061085 A2 | 5/2012 |
| WO | WO-2012120184 A2 | 9/2012 |
| WO | WO-2012138801 A2 | 10/2012 |
| WO | WO-2012138802 A1 | 10/2012 |
| WO | WO-2012151524 A2 | 11/2012 |
| WO | WO-2013083876 A2 | 6/2013 |

(56) References Cited

FOREIGN PATENT DOCUMENTS

| WO | WO-2013166469 A2 | 11/2013 |
|---|---|---|
| WO | WO-2013188401 A1 | 12/2013 |
| WO | WO-2014046826 A1 | 3/2014 |
| WO | WO-2014076612 A1 | 5/2014 |
| WO | WO-2014078120 A1 | 5/2014 |
| WO | WO-2014116173 A1 | 7/2014 |
| WO | WO-2014144746 A1 | 9/2014 |
| WO | WO-2014178911 A1 | 11/2014 |
| WO | WO-2014179777 A1 | 11/2014 |
| WO | WO-2016007550 A1 | 1/2016 |

OTHER PUBLICATIONS

Khunsupat, et al. Molecular Weight Distribution of Lignin. Presentation; Georgia Institute of Technology. 2014.
Li, et al. Interaction of Supercritical Fluids with Lignocellulosic Materials. Ind. Eng. Chem. Res. 1988; 27:1301-1312.
Nguyen, et al. Molecular weight in LignoAnalyse 1, "Is GPC applicable to lignin?". Rome, Forum 8, May 10-12, 2007.
Saake et al. A comparison of lignin polymer models (DHPs) and lignins by 31P NMR spectroscopy. Phytochemistry. vol. 43, Issue 2, Sep. 1996, pp. 499-507.
Bridgwater. Review of fast pyrolysis of biomass and product upgrading. Biomass and Bioenergy. 2012; 38:68-94.
Co-pending U.S. Appl. No. 15/593,752, filed May 12, 2017.
Guerra, et al. Comparative evaluation of three lignin isolation protocols for various wood species. J Agric Food Chem. Dec. 27, 2006;54(26):9696-705.
Guerra, et al. Toward a better understanding of the lignin isolation process from wood. J Agric Food Chem. Aug. 9, 2006;54(16):5939-47.
Hu, Thomas Q. Recent Advances in the Isolation and Analysis of Lignins and Lignin—Carbohydrate Complexes. Characterization of Lignocellulosic Materials. Copyright © 2008 Blackwell Publishing Ltd. Published Online: Mar. 3, 2009. pp. 148-170. DOI: 10.1002/9781444305425.ch9.
Nanayakkar et al. Understanding the Degree of Condensation of Phenolic and Etherified C-9 Units of in Situ Lignins. Journal of Agricultural and Food Chemistry. vol. 59. 12514-12519.
Pakarinen, et al. Evaluation of preservation methods for improving biogas production and enzymatic conversion yields of annual crops. Biotechnol Biofuels. Jul. 19, 2011;4(1):20. doi: 10.1186/1754-6834-4-20.
Pinoresinol compound information, SciFinder Scholar, downloaded Sep. 29, 2017, 3 pages.
Roy et al. Short and Stereoselective Total Synthesis of Furano Lignans (±)-Dihydrosesamin, (±)-Lariciresinol Dimethyl Ether, (±)-Acuminatin Methyl Ether, (±)-Sanshodiol Methyl Ether, (±)-Lariciresinol, (±)-Acuminatin, and (±)-Lariciresinol Monomethyl Ether and Furofuran Lignans (±)- Sesamin, (±)-Eudesmin, (±)-Piperitol Methyl Ether, (±)-Pinoresinol, (±)-Piperitol, and (±)-Pinoresinol Monomethyl Ether by Radical Cyclization of Epoxides Using a Transition-Metal Radical Source. J. Org. Chem., 2002, 67 (10), pp. 3242-3248.
Sadeghifar, et al. Toward thermoplastic lignin polymers. Part 1. Selective masking of phenolic hydroxyl groups in kraft lignins via methylation and oxypropylation chemistries. Industrial & Engineering Chemistry Research 51.51 (2012):16713-16720.
Sadeghifar, et al. Understanding the Variables that Define Tg for Kraft Lignin and Procedure for its Determination. Departments of Chemistry and Forest Biomaterials. North Carolina State University. Raleigh, NC USA. 2012.
Sannigrahi, et al. Lignin structural modifications resulting from ethanol organosolv treatment of loblolly pine. Energy Fuel 2010; 24(1): 683-689.
Strassbreger, et al. The pros and cons of lignin valorisation in an integrated biorefinery. RSC Advances 4.48 (2014): 25310-25318.
Yamauchi et al. Effect of the benzylic structure of lignan on antioxidant activity. Biosci Biotechnol Biochem. Sep. 2007;71(9):2283-90.
Zoia, et al. Microwave-assisted lignin isolation using the enzymatic mild acidolysis (EMAL) protocol. J Agric Food Chem. Nov. 12, 2008;56(21):10115-22. doi: 10.1021/jf801955b. Epub Oct. 15, 2008.
Co-pending U.S. Appl. No. 15/965,639, filed Apr. 27, 2018.
Abacherli, et al. Lignin Analytical Cluster, "Towards Standardisation of Methods". Rome, Forum 8, May 10-12, 2007.
Acevedo, et al. Surface Activity of Lignin Fractions isolated by Organic Solvents. Powerpoint. 2005.
Asikkala, et. al. Accurate and reproducible determination of lignin molar mass by acetobromination. Journal of agricultural and food chemistry. 2012; 60:3968-3973.
Baker. Utilization of Sustainable Resources for Materials for Production of Carbon Fiber Structural and Energy Efficiency Applications. Oak Ridge National Laboratory, Tennessee, USA. Nordic Wood Biorefinery Conference, Stockholm, Sweden, Mar. 22-24, 2011.
Brauns et al. Studies on Lignin and Related Compounds: XII. Methanol Lignin. Canadian Journal of Research 13b(1):28-34 (1935).
Brauns, Friedrich Emil. The Chemistry of Lignin. Academic Press. 1952. pp. 66, 67, and 127.
Chaow-U-Thai et al. Removal of ash from sugarcane leaves and tops. International Journal of Biosciences.2012; 2(5): 12-17.
Chatterjee, et al. Lignin-Derived Advanced Carbon Materials. ChemSusChem. Dec. 2015;8(23):3941-58. doi: 10.1002/cssc.201500692. Epub Nov. 16, 2015.
Compere, et al. Evaluation of Lignin from Alkaline-Pulped Hardwood Black Liquor. Oak Ridge National Laboratory, US Department of Energy, under contract DE-AC05-000R22725, ORNLITM-2005/88. May 2005.
Compere, et al. Improving the fundamental properties of lignin-based carbon fiber for transportation application. Oak Ridge National Lab. 2009.
Compere, et al. Low cost carbon fiber from renewable resources. Carbon. 1998; 36(78):1119-1124.
Constantinescu, et al. Lignin hydrophobization by different esterification reactions. ILI—Forum 8, May 10-12, 2007.
Cui, et al. Toward thermoplastic lignin polymers; part II: thermal & polymer characteristics of kraft lignin & derivatives. BioResources 8.1 (2013): 864-886.
Economy, et al. Activated carbon fibers—past, present, and future. 1996; 321-358.
Finney, et al. Fuel Pelletization with a Binder: Part I—Identification of a Suitable Binder for Spent Mushroom Compost-Coal Tailing Pellets. Energy & Fuels, 2009, 23 (6), pp. 3195-3202.
Gabilondo, et al. Lignin low molar mass fractions involvement in the synthesis of PF matrices. 2007.
Glasser. Lignin retrospect and prospect. 2010.
Gosselink, et al. Analysis of isolated lignin samples using organic and alkaline SEC and MALDI-TOF-MS. Agrotechnology & Food Sciences Group. 2006.
Gosselink, et al. Analytical protocols for characterisation of sulphur-free lignin. Industrial Crops and Products. 2004; 19:271-281.
Gosselink, et al. Co-ordination network for lignin—standardisation, production and applications adapted to market requirements (EUROLIGNIN). Industrial Crops and Products 2004; 20:121-129.
Gosselink, et al. Lignin depolymerization under supercritical process conditions. Agrotechnology & Food Sciences Group. 2008.
Griffith, et al. Low cost carbon fiber for transportation application. USDE. 2003.
Guerra, et al. On the Propensity of Lignins to Associate. Organic Chemistry of Wood Components Laboratory Department of Forest Biomaterials Science & Engineering North carolina State Raleigh, North Carolina USA. 2007.
Hage, et al. Effects of process severity on the chemical structure of Miscanthus ethanol organosolv lignin. Polymer Degradation and Stability. 2010; 95:997-1003.
Hagglund. Hydrochloric acid lignin (preliminary communication). Berichte der Deutschen Chemischen Gesellschaft [Abteilung] B: Abhandlungen (1923), 56B 1866-8. CODEN: BDCBAD ISSN: 0365-9488. Abstract only.

(56) References Cited

OTHER PUBLICATIONS

Hallac, et al. Biomass Characterization and Organosolv Pretreatment of Buddleja davidii. School of Chemistry and Biochemistry, Institute of Paper Science and Technology, Georgia Institute of Technology, Atlanta, GA. 2009.

Hallac, et al. Biomass Characterization of Buddleja davidii: A Potential Feedstock for Biofuel Production. J. Agric. Food Chem. 2009; 57(4):1275-1281.

Hallac, et al. Chemical Transformations of Buddleja davidii Lignin during Ethanol Organosolv Pretreatment. Energy Fuels. 2010; 24:2723-2732.

Hallac. Fundamental understanding of the biochemical conversion of buddleja davidii to fermentable sugars. Georgia Institute of Technology. May 2011.

Harris. Derived products and chemical utilization of wood waste. Forest Products Laboratory; Forest Service US Department of Agriculture; Rept. No. R1666-10. Jun. 1949.

Holladay, et al. Top Value-Added Chemicals from Biomass vol. II—Results of Screening for Potential Candidates from Biorefinery Lignin. Pacific Northwest National Laboratory, Prepared for the U.S. Department of Energy. Oct. 2007.

Ibarra, et al. Isolation of high-purity residual lignins from eucalypt paper pulps by cellulase and proteinase treatments followed by solvent extraction. Enzyme and Microbial Technology. 2004; 35:173-181.

International search report and written opinion dated Sep. 30, 2015 for PCT/US2015/039438.

Kadla, et al. Lignin-based carbon fibers for composite fiber applications. Carbon. 2002; 40:2913-2920.

Koullas, et al. Analytical methods for lignin characterization—differential scanning calorimetry. Cellulose Chem. Technol. 2006; 40(9-10):719-725.

Kubo, et al. Lignin-based Carbon Fibers: Effect of Synthetic Polymer Blending on Fiber Properties. Journal of Polymers and the Environment. Apr. 2005; 13(2):97-105.

Kubo, et al. Poly(Ethylene Oxide)/Organosolv Lignin Blends: Relationship between Thermal Properties, Chemical Structure, and Blend Behavior. Macromolecules. 2004; 37:6904-6911.

Kubo, et al. Preparation of carbon fibers from softwood lignin by atmospheric acetic acid pulping. Carbon. 1998; 36(7-8):1119-1124.

Kubo, et al. Surface Porosity of Lignin/PP Blend Carbon Fibers. Journal of Wood Chemistry and Technology. 2007; 27: 257-271.

Kubo, et al. Thermal Decomposition Study of Isolated Lignin Using Temperature Modulated TGA. Journal of Wood Chemistry and Technology. 2008; 28(2):106-121.

Kudahettige-Nilsson, et al. Biobutonal production by clostridium acetobutylicum using xylose recovered from birch kraft black liquor. Bioresource Technology. 2015; 176:71-79.

Lange, et al. On the imlicatiions of calibration techniques and detector systems on GPC-based analyses of lignin. Cost action FP 0901 (presentation), 2013.

Liitia, et al. Application of Solid-State $^{13}$C NMR Spectroscopy and Dipolar Dephasing Technique to Determine the Extent of Condensation in Technical Lignins. Solid State Nuclear Magnetic Resonance. 2002; 21:171-186.

Lin and Dence (Eds), Methods in lignin chemistry. Springer Berlin Heidelberg, 1992, p. 208.

Lora, et al. Recent Industrial Applications of Lignin: A Sustainable Alternative to Nonrenewable Materials. Journal of Polymers and the Environment, Apr. 2002; 10(1-2):39-48.

Lora, et al. Use of sulfur-free lignin in wood adhesives: Industrial experiences and environmental impacts. 2005; 8-14.

Lora. Lignin recovery technology transfer: first industrial implementation of the LPS process in India. 2005.

Marcano, et al. Surface activity of lignin fractions obtained at different pH values. 2005.

Nguyen, et al. Is gel permeation chromatography applicable to lignin? 2007.

Nguyen, et al. Molecular weight and functional group analysis of a Soda lignin fractionated by ultrafiltration and selective dissolution. 2008.

Pepper, et al. The effect of initial acid concentration on the lignin isolated by the acidolysis of aspen wood. Can J. Chem. 1961; 39:1454-1461.

Ragauskas, et al. From wood to fuels Integrating biofuels and pulp production. Industrial biotechnology. 2006; 2(1):55-65.

Ragauskas. Rediscovering the Future of Lignin Chemistry. 2003.

Reinhold. SEC of lignins. Mainz, Germany. 2007.

Sadeghifar, et al. Macroscopic Behavior of Kraft Lignin Fractions: Melt Stability Considerations for Lignin—Polyethylene Blends. ACS Sustainable Chem. Eng., 2016, 4 (10), pp. 5160-5166. DOI: 10.1021/acssuschemeng.6b00636.

Sadeghifar, et al. Toward Carbon Fibers from Single Component Kraft Lignin Systems: Optimization of Chain Extension Chemistry. ACS Sustainable Chem. Eng., 2016, 4 (10), pp. 5230-5237. DOI: 10.1021/acssuschemeng.6b00848.

Samuel, et al. Structural Characterization and Comparison of Switchgrass Ball-milled Lignin Before and after Dilute Acid Pretreatment. Appli. Micr. BioTech. 2010, 162:62-74.

Shen, et al. Lignin-Based Activated Carbon Fibers and Controllable Pore Size and Properties. Journal of Applied Polymer Science. 2011; 121:989-994.

Sudo, et al. A New Modification Method of Exploded Lignin for the Preparation of a Carbon Fiber Precursor. Journal of Applied Polymer Science. 1993; 48:1485-1491.

Svensson. Minimizing the sulfur content in Kraft lignin. Degree Project, ECTS 30.0,At STFI-Packforsk, Stockholm, 2008.

Toledano, et al. Characterization of key functional groups of lignin. 5th Italian meeting on lignocellulosic chemistry. Sep. 1-4, 2009—Villa Monastero Varenna (Lecco) Italy.

Toledano, et al. Study of fractionation of lignin by ultrafiltration and selective recipitation. 2009.

Uraki, et al. Preparation of activated carbon fibers with large specific surface area from softwood acetic acid lignin. J Wood Sci. 2001; 47:465-469.

Velez, et al. Temperature effects on molecular properties of liquid lignin recovered from kraft black liquor. ACS Sustainable Chem. Eng. 2015; 3:1032-1038.

Wang, et al. Molecular Characteristics of Kraft-AQ Pulping Lignin Fractionated by Sequential Organic Solvent Extraction. Int. J. Mol. Sci. 2010; 11:2988-3001.

Warren. Future Lower Cost Carbon Fiber for Autos: International Scale-up & What is Needed. Oak Ridge National Laboratory, Tennessee, USA. 2007.

Yang, et al. Alcohol adsorption on softwood lignin from aqueous solutions. Biotechnol Bioeng. Feb. 5, 1990;35(3):268-78.

Zhao, et al., Organosolv pretreatment of lignocellulosic biomass for enzymatic hydrolysis, Appl Microbiol Biotechnol (2009) 82:815-827.

Balakshin et a. On the Quantification of Lignin Hydroxyl Groups With 31P and 13C NMR Spectroscopy. Journal of Wood Chemistry and Technology 35(3):220-237 (Apr. 21, 2015).

Beall. Thermogravimetric Analysis of Wood Lignin and Hemicelluloses. Wood and Fiber Science, No. 3, pp. 215-226 (1969).

Co-pending U.S. Appl. No. 16/157,745, filed Oct. 11, 2018.

Co-pending U.S. Appl. No. 16/223,720, filed Dec. 18, 2018.

Gosselink et al. Fractionation, analysis, and PCA modeling of properties of four technical lignins for prediction of their application potential in binders. Holzforschung, vol. 64, pp. 193-200 (2010).

Gosselink. Lignin as a renewable aromatic resource for the chemical industry. PhD Thesis, Wageningen University, Wageningen, NL (2011). 194 pages.

Hui et al. Quantitative 31P NMR Analysis of Lignocellulosic Materials in Ionic Liquids. Chem Res Chinese Universities 26(3):488-490 (2010).

Ni et al. Alcell Lignin Solubility in Ethanol-Water Mixtures. Journal of Applied Polymer Science, vol. 57, pp. 1441-1446 (1995).

Reported CHO Ratios for Lignins. Technical Reviews, Chemical and Biomolecular Engineering, The University of Tennessee, Knoxville. Accessed Feb. 12, 2019 at URL:<http://biorefinery.utk.edu/ragauskas_tech_reviews.html>.

(56) References Cited

OTHER PUBLICATIONS

Vallejos et al. Chemical and physico-chemical characterization of lignins obtained from ethanol-water fractionation of bagasse. BioResources. 2011; 6: 1158-1171.
Vishtal et al. Challenges in Industrial Applications of Technical Lignins. BioResources 6(3):3547-3568 (2011).
Adler. Lignin Chemistry—Past, Present and Future. Wood Sci. Technol. 11:169-218 (1977).
Freudenberg et al. Constitution and Biosynthesis of Lignin pp. 82-84, 113, 118 (1968).
Jacquet et al. Thioacidolysis of Enzymatic Dehydrogenation Polymers from p-Hydroxyphenyl, Guiacyl, and Syringyl Precursors. Holzforschung 51:349-354 (1997).
Brodin et al. Kraft lignin as feedstock for chemical products: The effects of membrane filtration. Holzforschung 63:290-297 (2009).
Co-pending U.S. Appl. No. 16/426,936, filed May 30, 2019.
Co-pending U.S. Appl. No. 16/539,366, filed Aug. 13, 2019.
Co-pending U.S. Appl. No. 16/564,169, filed Sep. 9, 2019.
EP19156741.1 Extended European Search Report dated Jul. 19, 2019.
McCarthy et al. "Chapter 1: Lignin Chemistry, Technology, and Utilization: A Brief History," in Glasser et al. Lignin: Historical, Biological, and Materials Perspective (1999).
Phillips et al. The Chemistry of Lignin. 14 Chemical Reviews 103 (1934). 68 pages.
Product Specification. Product Name: Lignin, alkali—low sulfonate content, Product Number: 471003, CAS Number: 8068-05-1 (2008). Sigma-Aldrich, Saint Louis, MO, USA. One page.
Svensson. Minimizing the sulphur content in Kraft lignin. Degree Project, ECTS 30.0 at STFI-Packforsk, Stockholm (2008). 39 pages.
Zhang et al. Reaction Kinetics of the Hydrothermal Treatment of Lignin. Appl Biochem Biotechnol 147:119-131 (2008). Published online Oct. 23, 2007.
Caron, ed. General Solvent Properties. Practical Synthetic Organic Chemistry: Reactions, Principles, and Techniques, First Edition, John Wiley & Sons, Inc., pp. 805-818 (2011).
Co-pending U.S. Appl. No. 16/739,462, filed Jan. 10, 2020.
Co-pending U.S. Appl. No. 16/818,627, filed Mar. 13, 2020.
Zubrick. Extraction and Washing. The Organic Chem Lab Survival Manual: A Student's Guide to Techniques, John Wiley & Sons, pp. 111-114 (1988).

\* cited by examiner

US 10,767,308 B2

METHODS FOR SEPARATING AND REFINING LIGNIN FROM BLACK LIQUOR AND COMPOSITIONS THEREOF

CROSS REFERENCE TO RELATED APPLICATION

This application is a National Stage Entry of PCT/US2015/039438, filed Jul. 7, 2015, which claims the benefit of U.S. Provisional Application No. 62/022,644, filed Jul. 9, 2014, each incorporated herein by reference in its entirety.

FIELD OF THE INVENTION

The invention relates to separation and refining of lignin from spent cooking liquor (i.e., black liquor) present in industrial chemical plants.

BACKGROUND OF THE INVENTION

Removing a fraction of the lignin from black liquor allows pulp and paper mills that have reached the maximum throughput of their recovery boilers to increase production proportional to the fraction of lignin removed. For example, a large paper mill recovering 30% of their lignin from black liquor allows the mill to increase the overall production rate approaching that same percentage.

Lignin is also a valuable material for production of "green chemicals." The value of the lignin can increase even further if the lignin can be refined to a high degree by separating it effectively from ash and desulfurizing the covalently bound sulfite and sulfonate groups it acquires in the pulping process. PCT/US2013/039585 and PCT/US2013/068824 (both incorporated herein by reference for all purposes) disclose processes and methods to refine lignin to high purity by extracting it into a limited-solubility solvent and polishing the lignin in the organic phase by contacting with a strong acid cation exchange resin.

SUMMARY OF THE INVENTION

In one aspect, provided herein is a process for separating black liquor into at least two, three, or four streams selected from: (i) a gaseous stream comprising volatile sulfur compounds; (ii) a lignin-comprising stream produced by extracting lignin into a limited-solubility solvent S1; (iii) a salt stream, comprising solid sodium and sulfate salts; and (iv) a salt-depleted and lignin-depleted aqueous stream comprising hydrocarbons.

In another aspect, provided herein is a process for refining lignin from black liquor, the process comprising the steps of: (i) contacting black liquor with a limited-solubility solvent S1, thereby forming a solution; (ii) neutralizing the solution by addition of $CO_2$; (iii) separating precipitated salt from the solution; (iv) further acidifying the solution with mineral acid to a pH of at least 0.5 to at most 3.0; (v) separating the solution into a solvent S1 phase and an aqueous phase; and (vi) removing ash from the solvent S1 phase by contacting with a strong acid cation exchange resin; thereby obtaining a refined solution of lignin in the solvent S1 phase. In some examples, the process may further comprising one, two, three or four additional step(s) selected from: (i) distilling or flash evaporating the solvent S1 phase, thereby removing the bulk of the limited-solubility solvent S1 to obtain a solid lignin; (ii) heating the solid lignin to remove trace limited-solubility solvent S1 or water from the solid lignin; (iii) applying a vacuum to the solid lignin to remove trace limited-solubility solvent S1 or water from the solid lignin; (iv) dissolving the solid lignin in an organic solvent to form a resultant suspension; and (v) separating the insoluble remainder from the suspension. The black liquor may be a product of a kraft pulping process.

In practicing any of the processes described herein, the lignin may be desulfurized by reacting it in solvent S1 with a reducing agent in the presence of a catalyst and a hydrogen donor. In some examples, the hydrogen donor is 2-butanol, and 2-butanone is produced as a byproduct of the desulfurization.

In another aspect, provided herein is a process to produce methane by anaerobic digestion of a salt-depleted and lignin-depleted aqueous stream prepared by a process described herein.

In another aspect, the invention provides a lignin composition comprising: (i) less than 3.2% sulfur (wt/wt); (ii) trace S1 solvent; and (iii) a black liquor residue; wherein the black liquor residue is present in an amount of at most 10000 ppm, at most 9000 ppm, at most 8000 ppm, at most 7000 ppm, at most 6000 ppm, at most 5000 ppm, at most 4000 ppm, at most 3000 ppm, at most 2000 ppm, at most 1000 ppm, at most 500 ppm, at most 100 ppm, at most 50 ppm, at most 10 ppm, or less than 10 ppm (wt/wt).

In yet another aspect, provided herein is an industrial-scale chemical plant comprising black liquor, wherein the plant is configured to separate lignin from the black liquor via extraction with a limited-solubility S1 solvent, and wherein the chemical plant does not comprise a recovery boiler. In some examples, the plant is configured to produce lignocellulosic material, paper, cardboard, purified lignin, or combinations thereof. The chemical plant may be configured to recycle black liquor, wherein lignin is separated from the black liquor and the black liquor is not concentrated.

In another aspect, provided herein is a process for separating lignin from black liquor, the process comprising the steps of: (i) contacting the black liquor with a limited-solubility solvent, thereby forming a mixture; (ii) neutralizing the mixture by addition of $CO_2$; (iii) filtering the mixture, thereby generating a filtrate and a filtration cake; (iv) acidifying the filtrate; (v) separating the filtrate into an organic phase and an aqueous phase; (vi) removing metal cations from the organic phase; and (vii) recovering lignin from the organic phase. In some examples, the limited-solubility solvent may comprise a 4- to 8-carbon ketone, for example, methyethyl ketone. In some examples, the contacting the black liquor with the limited-solubility solvent induces precipitation of a salt. In some examples, the salt comprises a carbonate, bicarbonate, sulfate, or bisulfate ion.

In practicing any of the processes described herein, the mixture may be maintained at a temperature of at least 30° C. to at most 90° C. during the addition of $CO_2$. In some examples, the addition of $CO_2$ is halted once the mixture has a pH of at least 7.1 to at most 9.5. The mixture may be stirred for at least 20 minutes after the addition of $CO_2$ to allow for salt formation. In some examples, the filtrate is acidified by addition of an acid, for example, a mineral acid (e.g., sulfuric acid). The acidification may cause further precipitation of a salt. In some examples, the precipitate is removed by filtration.

In practicing any of the processes described herein, the recovering lignin from the organic phase may occur by evaporation of the organic phase, thereby forming a solid lignin. This may comprise contacting the organic phase with water at an elevated temperature, thereby forming a lignin precipitate. The solid lignin may be collected by filtering the lignin precipitate. In some examples, the solid lignin is dried by application of a vacuum to the solid lignin. The solid lignin may be dissolved in an organic solvent.

In practicing any of the processes described herein, the organic phase may undergo a desulfurization reaction. Solid lignin dissolved in an organic solvent may undergo a desulfurization reaction. In some examples, the desulfurization reaction comprises a desulfurization catalyst, including, for example, Raney nickel, $MoS_2$, $CoS_2$, or a combination thereof. In some examples, the desulfurization reaction further comprises the addition of a hydrogen donor, for example, an alcohol (e.g., 2-butanol). The desulfurization reaction may be conducted at a temperature of at least 50° C. to at most 200° C. In some examples, the desulfurization reaction is conducted at a pressure of at least 1 mPa to at most 30 mPa. Following the desulfurization reaction, the organic phase may optionally be filtered.

In practicing any of the processes described herein, the neutralizing step may induce precipitation of carbohydrates. Optionally, the filtration cake is contacted with the aqueous phase of the acidified filtrate, thereby forming a slurry. In some examples, the slurry is acidified to a pH of at least 0.5 to at most 3.0. The slurry may be heated to a temperature of at least 80° C. to at most 150° C. In some examples, at least 50% of precipitated carbohydrates in the slurry are converted to water-soluble carbohydrates. An aqueous solution suitable for anaerobic digestion may be separated from the slurry. This aqueous solution suitable for anaerobic digestion may comprise less than 400 ppm calcium. In some examples, the aqueous solution suitable for anaerobic digestion comprises less than 2,000 ppm sulfur. The aqueous solution suitable for anaerobic digestion may have a chemical oxygen demand (COD) value of at least 35,000. Optionally, the aqueous solution suitable for anaerobic digestion undergoes an anaerobic digestion to produce methane, for example, using a microorganism. The methane produced may be used as an energy source.

In practicing any of the processes described herein, removing metal cations from the organic phase may comprise contacting the organic phase with a strong acid cation exchange resin.

In one aspect, provided herein is a lignin composition comprising at least 80% lignin (wt/wt) and one, two, three, or four additional characteristics selected from: (i) sulfur in an amount up to 3.2% (wt/wt); (ii) ash in an amount up to 1% ash (wt/wt); (iii) polyvalent cations in an amount up to 500 ppm, relative to lignin; and (iv) carbohydrates in an amount up to 500 ppm carbohydrates, relative to lignin. In some examples, the lignin composition may comprise less than 1.6% sulfur (wt/wt).

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Where a series of values is provided, it is understood that each recited value encompasses a value range from at most ten percent (i.e., a tenth of a unit) more than the recited value to at least ten percent less than the recited value, unless the context clearly dictates otherwise. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Black liquor can be removed from the pulp mill's recovery plant downstream of an efficiently performing soap separator removing tall oils. Tall oils comprise chemicals of high value and may be recovered by suitable processes. One aspect of the current invention is to separate lignin and salts from the remaining black liquor and to optimize the yield of energy from this stream. The term "black liquor" refers to a liquid byproduct of the kraft process during the production of paper pulp. Black liquor comprises an aqueous solution of lignin residues, hemicellulose, and inorganic residues. Saponified tall oils may be skimmed off the surface of crude black liquor, leaving behind "weak black liquor" comprising about 10% to about 30% dissolved solids, wherein lignin comprises from about 25% to about 45% of the solids. Black liquor may be concentrated to increase the solids to more than 30% wt/wt, more than 40% wt/wt, more than 50% wt/wt, more than 60% wt/wt, more than 70% wt/wt, or even more than 80% wt/wt. Relative amounts of lignin, carbohydrates, inorganic solutes and the specific composition may vary significantly depending on the biomass feedstock and milling processes.

Figure 1A:
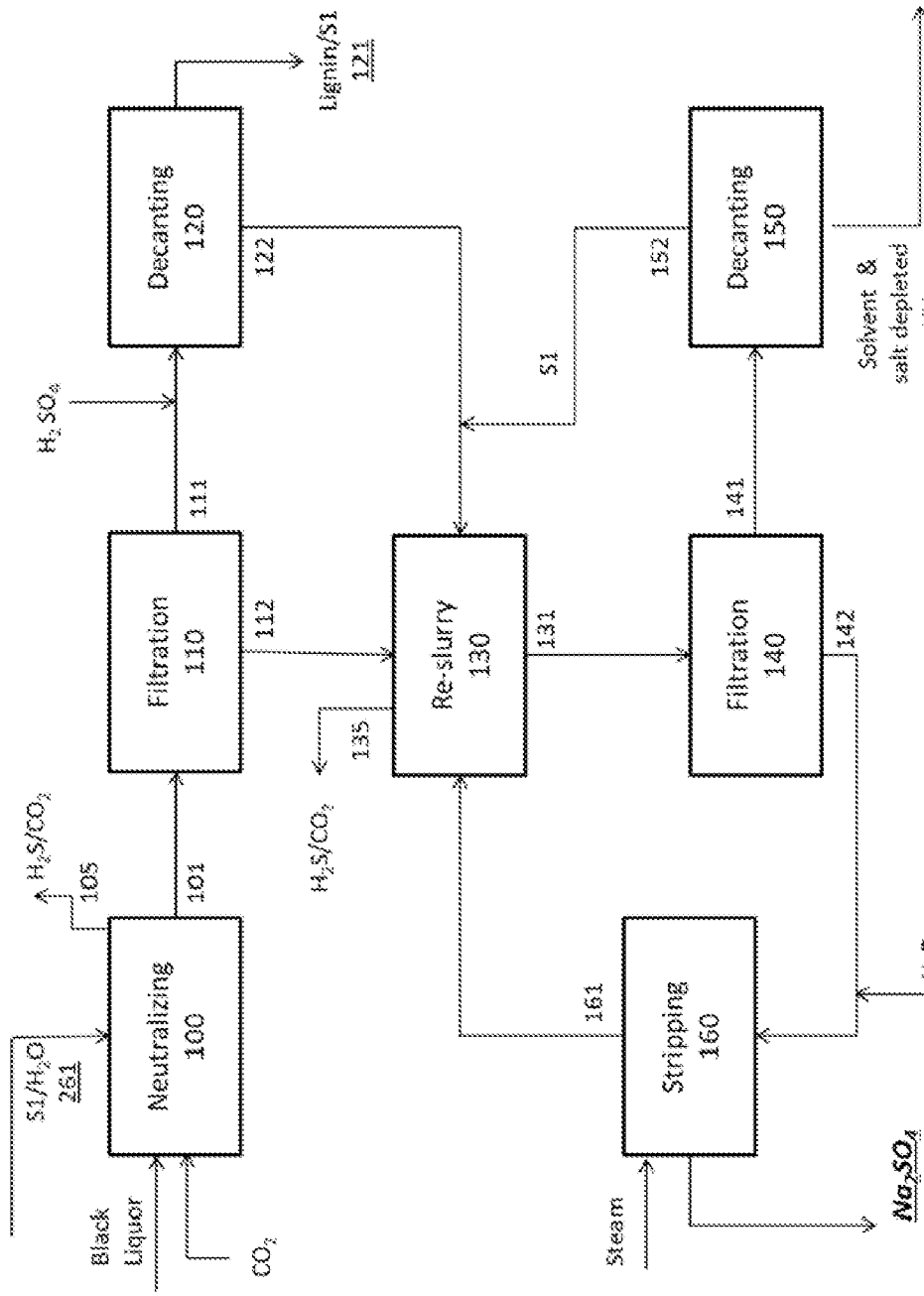
FIG. 1A is a schematic representation of a simplified process scheme of the separation of lignin from black liquor into a limited solubility solvent, and the reduction of sulfate salt loads from the remaining aqueous stream.
Figure 1B:
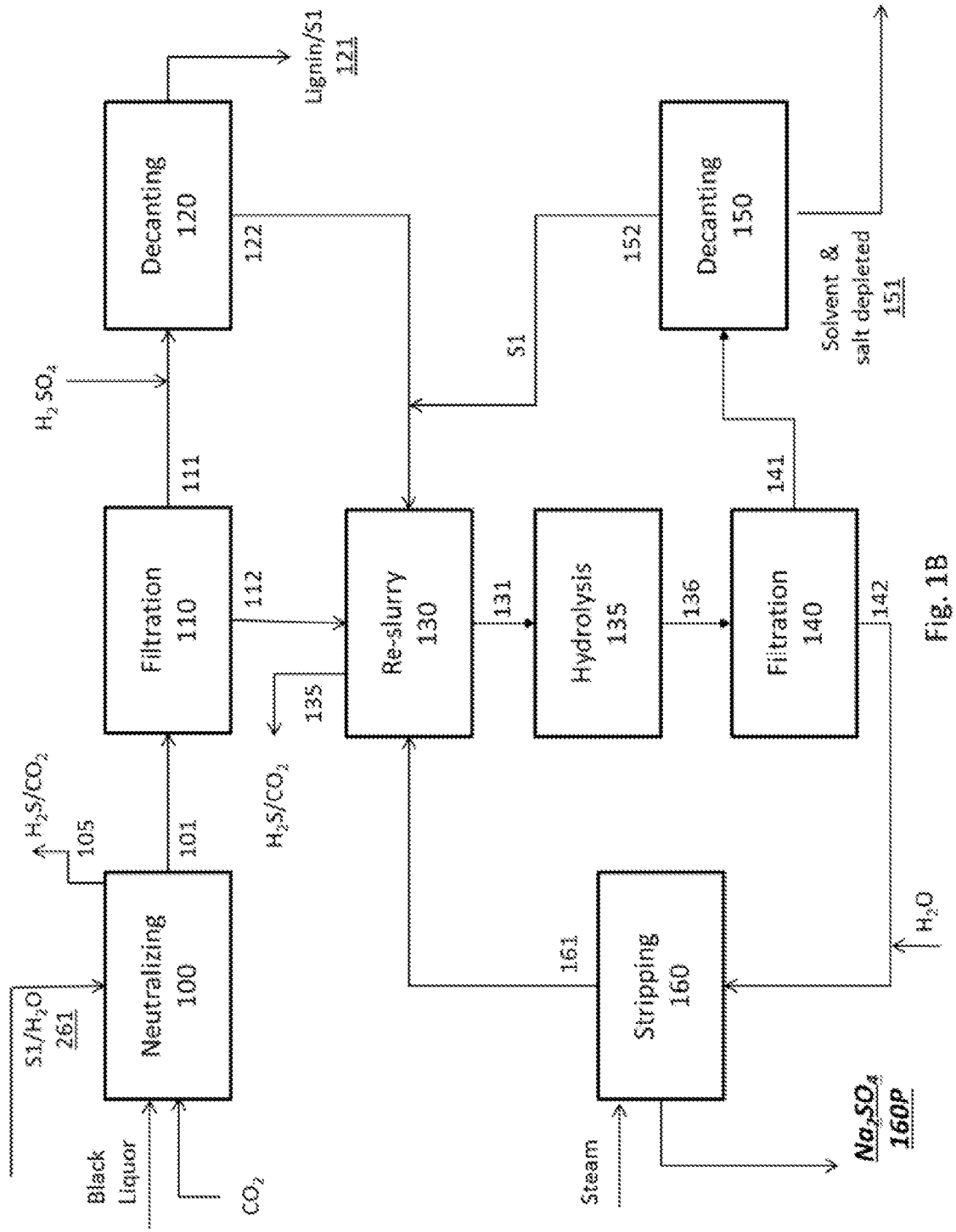
FIG. 1B is an alternative schematic representation of a simplified process scheme of the separation of lignin from black liquor into a limited solubility solvent, and the reduction of sulfate salt loads from the remaining aqueous stream.
Figure 2:
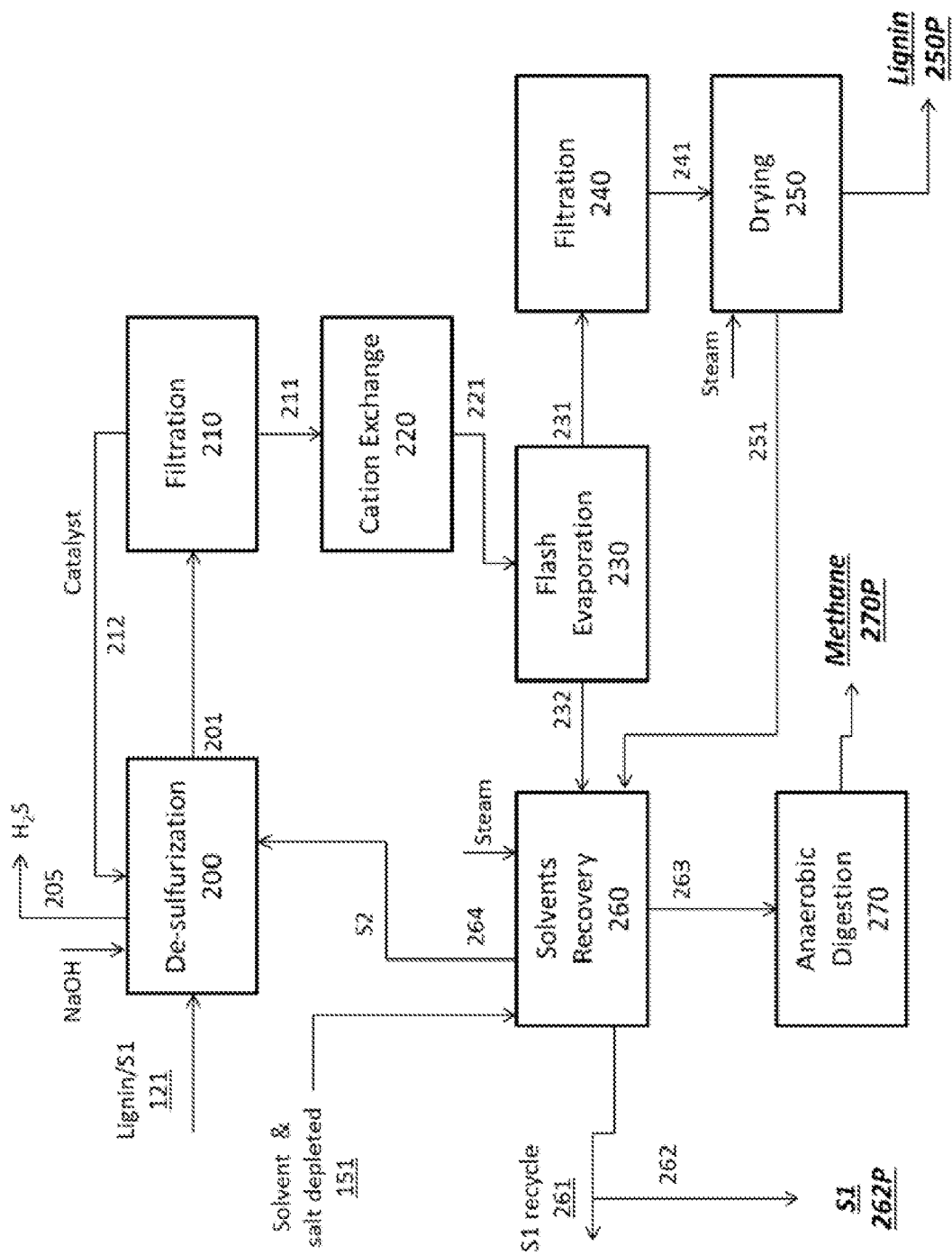
FIG. 2 is a schematic representation of a process scheme of lignin desulfurization and refining, including solvent recycling and anaerobic digestion of the organic load of aqueous streams to methane.

The process to separate and refine lignin from black liquor, to separate inorganic salts, and to utilize the organic matter remaining in the aqueous stream to produce methane, is shown schematically in FIGS. 1A, 1B and 2. In some embodiments, the process comprises two parts: (i) lignin separation from salts and carbohydrates and (ii) lignin refining. These two parts of the process are described in further detail below. The refined lignin can be separated from the limited-solubility solvent by well-known methods of flash evaporation.

The presently disclosed methods enable the removal of the high salt load typically obtained when neutralizing black liquor by acidification and handling the toxic emission of hydrogen sulfide gas which is emitted upon neutralizing, preferably while capturing the gas for reuse at the paper mill. Effective removal of the high salt formed upon acidification can allow further harvesting of energy from the salt depleted and lignin depleted aqueous stream, which still contains a high load of hemicellulose polymers, oligomers and monomers as well as hydrated sugar species (e.g., furfural and its derivatives), extractives and organic acids. Once salts and lignin have been removed, this stream can be digested anaerobically to produce methane, thus maximizing the use of this paper mill effluent stream.

Lignin Separation

FIG. 1A depicts certain embodiments of lignin and salt separation as described herein. In some embodiments, highly basic black liquor is first neutralized (100) by sparging the solution with $CO_2$ in a biphasic aqueous/organic solution, where the organic phase comprises a limited solubility solvent S1. Gases can optionally be vented (105) and collected for recycling of sulfur volatiles, such as for use at a paper mill. Recycling can be accomplished by reducing sulfur volatiles to $H_2S$ or oxidizing sulfur volatiles to sulfuric acid for use in the refining process of the current invention. In some aspects, lignin can be extracted into the organic phase, in which the resulting aqueous phase comprises limited solubility solvent having reduced salt solubility and reduced hemicellulose oligomers solubility. In some embodiments, a portion of the inorganic solutes can be precipitated due to the reduced salt solubility in the aqueous phase. In some embodiments, at least 25, 30, 35, 40, 45, 50, 55, 60, 65 or at least 70% of the inorganic solutes are precipitated due to reduced salt solubility in the aqueous phase comprising the limited solubility solvent (i.e., the S1 solvent). In some embodiments, at most 30, 35, 40, 45, 50, 55, 60, 65 or at most 70% of the inorganic solutes are precipitated due to reduced salt solubility in the aqueous phase comprising the limited solubility solvent (i.e., the S1 solvent). In some embodiments, a portion of the hemicellulose oligomers are precipitated due to the reduced solubility in neutralized solvent saturated aqueous phase. Such oligomers may comprise oligoxylans, oligo-mannans, glucomannans, galactomannans, any other carbohydrate species present as an oligomer, or mixtures thereof. In some embodiments, at least 50, 55, 60, 65, 70, 75, 80 or at least 85% of carbohydrate oligomers are precipitated in the neutralized solvent saturated aqueous phase. In other embodiments, at most 50, 55, 60, 65, 70, 75, 80 or at most 85% carbohydrate oligomers are precipitated in the neutralized solvent-saturated aqueous phase.

The resulting precipitate 101, comprising salts and carbohydrates, can be removed from the suspension by at least one method known in the art. For example, in some embodiments the salts are removed via filtration 110. In some embodiments, the salts are filtered (110) by simple filtration. The recovered salts can be transferred (112) to a re-slurry tank 130. In some embodiments, the filtrate 111 is acidified. For example, the filtrate can have the pH adjusted to at most 8, 7, 6, 5, 4, 3 or to at most 2. For example, the filtrate can have the pH adjusted to at least 7, 6, 5, 4, 3, or to at least 1. In some cases, the pH is adjusted using sulfuric acid ($H_2SO_4$) or other suitable acid. In some embodiments, the filtrate pH is adjusted to a pH of at least 2.3 and not more than 3.0 by the addition of $H_2SO_4$. In some cases, the filtrate pH is adjusted to a pH of at least 2.5 and not more than 3.7 by the addition of $H_2SO_4$. In other embodiments, the filtrate pH is adjusted to a pH of at least 2.1 and not more than 3.9 by the addition of $H_2SO_4$. In some other embodiments, the filtrate is acidified with mineral acid to a pH of at least 0.5 to a pH of at most 3.0. The resulting organic and aqueous phases can be separated (120) by centrifuge or any other decantation or phase separation process, as would be known in the art. Stream 121, comprising lignin and solvent S1, can be optionally transferred to a lignin-refining region, while stream 122, comprising water, salts, organic acids, sugars and dehydrated sugars, can be directed to the re-slurry tank 130. In some aspects, the salt is re-slurried (130) at a temperature of at least 50° C. and at most 65° C. and adjusted to a pH of at least 2.5 and at most 3.0 with $H_2SO_4$. In some embodiments, the pH is adjusted to less than 2.5 with $H_2SO_4$. In some embodiments, the slurry is acidified to a pH of at least 0.5 to at most 3.0. In some embodiments, the solution is stirred for at least 10, 15, 20, 25, 30, 35, 40, 45, 50, 55 or at least 60 minutes. In other embodiments, the solution is stirred for at most 20, 25, 30, 35, 40, 45, 50, 55 or at most 60 minutes. In some embodiments, the acidified solution is further heated to affect hydrolysis of the oligomeric carbohydrates (135) either in the same vessel or in a different vessel. In some embodiments, hydrolysis 135 is affected by heating the slurry to a temperature of at least 80° C. and at most 150° C., optionally the temperature can be at least 90° C. and at most 120° C., for a period of 30-300 minutes, optionally 45-120 minutes. In some embodiments, the hydrolysis converts at least 50, 55, 60, 65, 70, 75, 80, 85 or at least 90% of the precipitated carbohydrates to water soluble carbohydrates. In some embodiments, the hydrolysis converts at most 50, 55, 60, 65, 70, 75, 80, 85 or at most 90% of the precipitated carbohydrates to water soluble carbohydrates.

In some embodiments, the resulting salts comprise primarily $Na_2SO_4$. In some aspects, the resulting salts (131 in FIG. 1A or 136 in FIG. 1B) are filtered 140. The remaining solvent can optionally be stripped (160), for example by steam, to recover a mixture of solvent S1 and water 161. In some embodiments, the $Na_2SO_4$ salt exits the stripper as a component of an aqueous solution in the absence (or near absence) of solvent S1, which can then be collected as a byproduct (160P). The filtrate stream 141 can be decanted 150, for example, by a suitable centrifuge or other phase separation device, to recover solvent S1 for optional further use in the process (stream 152). Stream 151, comprising water and residual amounts of solvent S1 and salt, can then be sent to solvent recovery 260.

Lignin Refining

FIG. 2 depicts lignin refining according to certain aspects of the present invention. As shown in FIG. 2, stream 121, comprising lignin and solvent S1, can be transferred to a desulfurization region 200. In some embodiments, the lignin and solvent S1 solution is stirred in a thermally controlled tank (200), and the pH is optionally adjusted to slightly basic, e.g., a pH of at least 7.5 to at most 8.0 by adding a suitable base, for example NaOH. In some examples, the pH is adjusted to slightly basic, i.e., pH of at least 7.2 to at most 7.5, 8.0, 8.5, 9.0, 9.5 or at most 10.0 by adding a base. The pH-adjusting base can be any suitable base, such as for example, NaOH, KOH, LiOH, $Mg(OH)_2$, $Ca(OH)_2$, or the like, or a combination thereof.

Following addition of a base, a catalyst for desulfurization can be added, such as for example Raney nickel, $MoS_2$, $CoS_2$, or a combination thereof. In further embodiments, a solvent S2 that acts as a reducing reagent (i.e., a hydrogen donor) is added, such as for example, an alcohol such as methanol, ethanol, isopropanol, 1-butanol, 2-butanol, or a combination thereof. The desulfurization processes for use according to the present disclosure can be selected from processes known in the petrochemical industry. As lignin is a highly aromatic polymer, catalytic chemistry can optionally be employed to remove sulfur from lignin polymer, analogously to removing sulfur functional groups from petrochemicals, such as petrochemical fractions rich in benzene, toluene, xylenes (BTX) and phenols of petrochemical sources. The vented gases comprising sulfur compounds can optionally be collected for recycling. The sulfur compounds can be either reduced to $H_2S$ (205), e.g., for return and use in a paper mill, or alternatively oxidized to sulfuric acid, e.g., for use in a process of the present disclosure.

Following desulfurization, the catalyst 201 can be filtered 210 and recycled (212) for further use. The filtrate stream 211 comprising lignin and solvent S1 can be treated as disclosed in PCT/US2013/039585 and PCT/US2013/068824. In such cases, the filtrate stream may first be refined (220) by contacting it with a strong acid cation exchange (SAC) resin in the $H^+$ form to capture remaining metal cations. According to some aspects of the present disclosure, pure lignin can be separated from the refined stream 221 by flash evaporation 230. In some embodiments, lignin separation from the refined stream may be achieved by contacting the S1 solution with water at a temperature sufficiently high such that it evaporates the solvent to which it is added. The S1 solvent evaporates when it has a boiling point below that of the added water. For example, in various aspects of the present disclosure, solvent S1 has a boiling point or azeotrope with water that boils at a temperature of at most 99, 95, 90, 85, 80, 75, 70, 65, 60, 55, 50° C. or less at ambient pressure. After removal of most or substantially all of the solvent S1 (232), the lignin can be collected as particles in water according to any suitable means. In some embodiments, solid lignin is filtered 240, and dried 250 to obtain a high purity solid lignin. Vapor streams 251 comprising solvent S1 and solvent S2 can be directed to a solvent recovery process 260 to optionally reuse these potentially valuable solvents.

Figure 3:
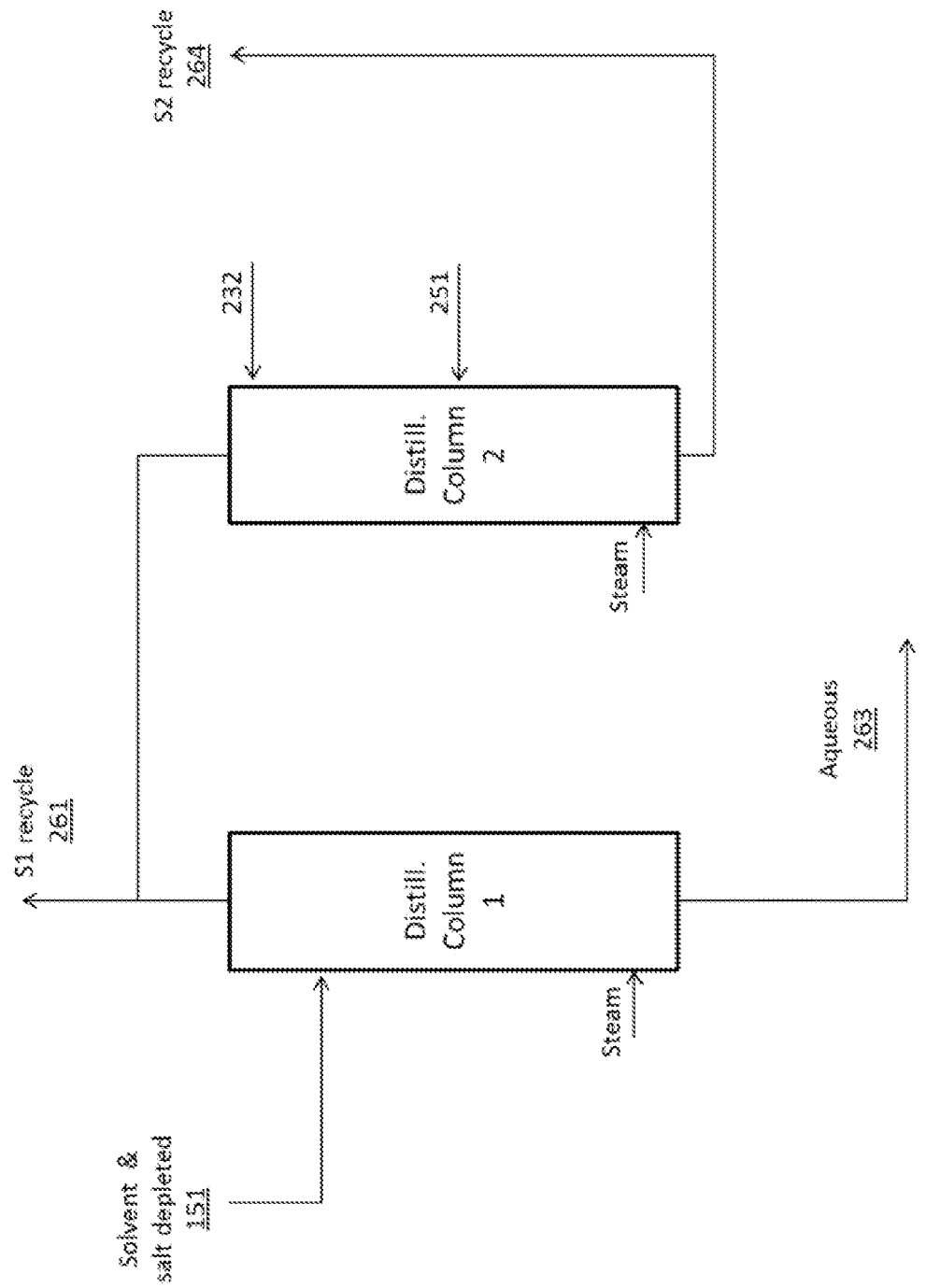
FIG. 3 is a schematic representation of a process scheme for purification of extractant comprising solvent recycling and distillation.

FIG. 3 depicts the recovery process 260 according to certain aspects of the present disclosure. Stream 151, comprising predominantly water as well as non-lignin dissolved organic matter, residual salts and solvent S1, can be fed into distillation column 1. In some embodiments, solvent S1 or its aqueous azeotrope is distilled off (261), leaving the aqueous phase (263) at the bottom. This phase may be suitable as a feed for anaerobic digestion 270. Suitable anaerobic feedstocks are generally characterized by low levels of sulfate and calcium salts (to avoid toxicity); low concentrations of phenolic lignin; and high chemical oxygen demand (COD), which can be attributed to carbohydrates and organic salts. Streams 232 from lignin filtration and 251 from lignin drying may be fed into distillation column 2, wherein solvent S1 can be distilled off (261) and solvent S2 (264) can optionally be collected from the bottom of the column. Both solvents may optionally be collected and recycled for further use. In some embodiments, the anaerobic digestion 270 can comprise microorganisms. In some examples, the microorganisms can include native (wild-type) or genetically modified anaerobic bacteria.

Reagents Recovery: each reaction tank may be equipped with vents so the gases comprising sulfur compounds or $CO_2$ can optionally be collected. In some embodiments, $CO_2$ is recycled for further use in the process for acidification of the next batch (e.g., as shown in FIG. 1a, 100). Gaseous sulfur compounds may also be collected (e.g., as shown in FIG. 1a, 105). The collected gaseous sulfur compounds can, e.g., be reduced to $H_2S$ for use in a paper mill and/or oxidized to produce the sulfuric acid required for the current process.

In some embodiments of the methods or processes described herein, the method or process eliminates the need to concentrate black liquor, thus reducing the energy input required and the high cost associated with having to concentrate the weak black liquor to strong black liquor before feeding it to the recovery furnace.

In some embodiments, the salt- and lignin-depleted aqueous stream (e.g., as shown in FIG. 2, 263) is digested to methane 270P in an anaerobic digester (270), thus eliminating partially or fully the need for a recovery furnace. In some examples, the methane is used as an energy source. In some embodiments, this elimination alleviates a bottleneck of current paper mills and allows for an increase in the capacity of an existing mill.

In some embodiments, high-purity lignin is produced as a result of the processes of the present disclosure. In some embodiments, the collection of solid high-purity lignin (250P) is done by flash evaporation 230 of solvent S1 followed by simple filtration 240. In further embodiments, the solid lignin is filtered from the aqueous phase. In certain aspects, the lignin produced according to the present processes has low ash content, low volatile material content, or a combination thereof. In further aspects, the lignin produced has low odor. In some embodiments, the lignin produced is sufficiently pure to be applied in applications that require extremely low ash and volatile material, and applications that call for low odor. In some embodiments the lignin produced comprises at most 3.5%, 3.0%, 2.0%, 1.0%, 0.5% or 0.25% wt/wt sulfur, at most 1%, 0.5% or at most 0.025% ash, or any combination of these specified sulfur and ash levels.

In some embodiments, the reagents used in the processes of the present disclosure are partially or fully recycled. In some embodiments, the recycled reagents include $CO_2$, $H_2SO_4$, solvent S1, solvent S2, or a combination thereof. In some embodiments, excess solvent S1 262 is produced in the reaction of S2, thereby increasing the quantity of S1 collected 262P.

Detailed Embodiments of Lignin and Salt Separation

In some embodiments, black liquor comprising at least 5% to at most 70% wt/wt dissolved solids, at least 15% to at most 50% wt/wt dissolved solids, or at least 20% to at most 25% wt/wt dissolved solids, is mixed with a limited-solubility solvent S1 and water to obtain a mixture comprising from about 30:70 to about 70:30 parts S1:water, about 40:60 to about 60:40 parts S1:water, about 55:45 to about 45:55 parts S1:water, or 55:45 parts S1:water. Any suitable limited-solubility solvent can be used according to the present disclosure. Non-limiting examples of limited-solubility solvents suitable for use with the present invention include methylethyl ketone, diethylketone, methyl isopropyl ketone, methyl propyl ketone, mesityl oxide, diacetyl, 2,3-pentanedione, 2,4-pentanedione, 2,5-dimethylfuran, 2-methylfuran, 2-ethylfuran, 1-chloro-2-butanone, methyl tert-butyl ether, diisopropyl ether, anisole, ethyl acetate, methyl acetate, ethyl formate, isopropyl acetate, propyl acetate, propyl formate, isopropyl formate, 2-phenylethanol, toluene, 1-phenylethanol, phenol, m-cresol, 2-phenylethyl chloride, 2-methyl-2H-furan-3-one, γ-butyrolactone, acetal, methyl ethyl acetal, dimethyl acetal, morpholine, pyrrole, 2-picoline, 2,5-dimethylpyridine, methyl tetrahydrofuran, dimethyl tetrahydrofuran, isopropyl ethyl ketone, diisopropyl ketone, and the like, or any combination thereof. Optionally, the limited-solubility solvent includes one or more of esters, ethers and ketones with 4 to 8 carbon atoms. For example, the limited-solubility solvent can include methyl acetate, ethyl acetate, propyl acetate, butyl acetate, pentyl acetate, hexyl acetate, heptyl acetate, alkyl acetate, aryl acetate, and the like, or any combination thereof, where the alkyl can be linear or branched. In some embodiments, an S1 solvent is an organic solvent that is at most 80, 70, 60, 50, 40, 30, 20, or at most 15% soluble in water. In other embodiments, an S1 solvent is an organic solvent that is at least 80, 70, 60, 50, 40, 30, 20, or at least 15% soluble in water.

The ratio of the limited-solubility solvent to water suitable for carrying out the lignin extraction can vary depending on the biomass material and the particular limited-solubility solvent used. In some embodiments, the solvent to water ratio can be in the range of from 100:1 to 1:100, e.g., from 90:1 to 1:90, from 80:1 to 1:80, from 70:1 to 1:70, from 60:1 to 1:60, from 50:1 to 1:50, from 40:1 to 1:40, from 30:1 to 1:30, from 20:1 to 1:20, or 1:1. In some embodiments, the solvent to water ratio is 1:1.

In some embodiments, the limited solubility solvent S1 is methylethyl ketone (MEK). MEK solubility in water at room temperature is about 28 g/100 ml and an azeotorope composition of about 80:20 with water. As disclosed in PCT/US2013/039585 and PCT/US2013/068824, MEK can be selected as an S1 solvent and can be an efficient solvent to extract lignin. In some embodiments, the S1 solvent can comprise MEK. In some embodiments, MEK is selected as the S1 solvent. In some embodiments of the present disclosure, the S1 solvent induces effective precipitation of salts present in neutralized black liquor. For example, the S1 solvent can induce precipitation of $Na_2CO_3$, $NaHCO_3$, $Na_2SO_4$, $NaHSO_4$, or any combination thereof from a liquor solution or suspension. In some examples, the S1 solvent can induce precipitation of $(alkali)_2CO_3$, $(alkali)HCO_3$, $(alkali)_2SO_4$ and $(alkali)HSO_4$ from a liquor solution or suspension, wherein "alkali" can be any alkali ion, for example, lithium (Li), sodium (Na), potassium (K), rubidium (Rb), caesium (Cs), francium (Fr), or any combination thereof. In some examples, contacting the black liquor with the limited-solubility solvent induces precipitation of a salt, for example, a salt comprising a carbonate, bicarbonate, sulfate, or bisulfate ion. In some embodiments, salts collected in the two filtration steps 110 and 140 comprise $Na_2CO_3$, $NaHCO_3$, $Na_2SO_4$, $NaHSO_4$, or any combination thereof. In some embodiments, the S1 solvent is also effective in inducing precipitation of substantially all salts present in neutralized black liquor at the prescribed concentration. Such salts can be those described herein or any other salt that is formed.

In some embodiments, the biphasic liquid is neutralized 100 by contacting with a $CO_2$ gas flow. In some embodiments, the $CO_2$ gas is bubbled through the solution (100) while the solution is stirred in a temperature controlled reactor at a temperature of at least 50° C. to at most 65° C. In some aspects, the temperature is at least 30, 40, 50, or at least 60° C. or more. In other aspects, the temperature is at most 40, 50, 60, 70, 80 or at most 90° C. or less. In some examples, the mixture is maintained at a temperature of at least 30° C. to at most 90° C. during the addition of $CO_2$. The bubbles can be large, medium, fine, or a combination thereof. In some embodiments, $CO_2$ is added until the pH of the aqueous phase is lowered to a pH of at least 7.5 to a pH of at most 7.7. In some embodiments, $CO_2$ is added until the pH of the aqueous phase is lowered to a pH of at least 7.1 to a pH of at most 9.5. In some embodiments, the solution is stirred further for at least 20, 30, 40, 50, 60, 70, 80, 90, 100, 110, 120, 130, 140, 150, 160, 170 or at least 180 minutes or more to allow for filterable salt formation. In some embodiments, the solution is stirred further for at most 20, 30, 40, 50, 60, 70, 80, 90, 100, 110, 120, 130, 140, 150, 160, 170 or at most 180 minutes or less to allow for filterable salt formation. In some embodiments, the salt is filtered 110 by any industrially common filtration device or process. In some embodiments, a filtration cake (112) is collected and characterized by loss on dry of at least 30, 35, 40, 45, 50 or at least 55% (wt/wt), where the dry substance may comprise at least 30, 40, 50, 60, 70, 80% of $NaHCO_3$, $Na_2CO_3$ or a combination of $NaHCO_3$ and $Na_2CO_3$. The loss on dry value for a given sample corresponds to the quantity of mass that is lost upon drying the sample. The solid 112 can also comprise relatively lower amounts of other metal salts of bicarbonate and/or carbonate, depending on the original composition of the black liquor. In some embodiments, the filtration cake comprises at least 10, 15, 20, 25, 30 or at least 40% of the salts present in the black liquor before acidification. In some embodiments, the dry substance in the filtration cake comprises at least 20, 30, 40, 50, or at least 60% wt/wt of carbohydrates, present as oligomers.

The filtrate (111) can be transferred to a temperature-controlled reactor, and the pH may be adjusted to a pH of at least 0.5 to at most 3.0 via addition of a suitable acid. The acid can be a mineral acid, for example, sulfuric acid. In some embodiments, the acid is sulfuric acid produced by oxidizing gaseous sulfur compounds collected from the vents of the reactors of the processes described herein. At this pH range (i.e, a pH of at least 0.5 to at most 3.0), the lignin can be extracted into the organic phase. The acidified solution may optionally be stirred for a time period of at least 1, 2, 3, 4, or at least 5 minutes after the desired pH is reached. The aqueous and organic phases can then be separated (120). In some embodiments, the separation is achieved by decanting, using a centrifuge, a hydrocylone or another suitable separation device. In some embodiments, light phase stream 121 comprising extracted lignin and solvent S1 is transferred to a lignin purification process.

In some embodiments, the filtration cake is re-slurried 130 in an aqueous solution comprising the lower phase of decanting 120 (i.e., stream 122). The pH may optionally be adjusted to reach a stable pH of at least 0.5 to at most 3.0, at least 1.5 to at most 3.0, or at least 2.5 to at most 3.0. In some embodiments, the acidification releases the carbonate ion as $CO_2$, which may be collected and recycled for further use in the process. In some embodiments, $Na_2SO_4$, $NaHSO_4$, or a combination of $Na_2SO_4$ and $NaHSO_4$ is precipitated due to the presence of limited solubility solvent S1 in the solution which may be adjusted as necessary to effect the precipitation. The slurry is optionally heated to a temperature of at least 80° C. and at most 150° C. (e.g., to at least 90° C. and at most 120° C.) for a period of 30-300 minutes (e.g., 45-120 minutes), to cause hydrolysis of the precipitated carbohydrate oligomers to aqueous-soluble carbohydrates (135). In some embodiments, the hydrolysis converts at least 50, 55, 60, 65, 70, 75, 80, 85 or at least 90% of the precipitated carbohydrates to water soluble carbohydrates. In some embodiments, the hydrolysis converts at most 50, 55, 60, 65, 70, 75, 80, 85 or at most 90% of the precipitated carbohydrates to water soluble carbohydrates.

The resulting salt precipitate can be filtered (140) by any industrially common filtration device or process. In some embodiments, a filtration cake 142 is collected, characterized by loss on dry of at least 35, 40, 45 or at least 50%, where the dry substance comprises at least 50, 60, 70 or at least 80% $NaHSO_4$, $Na_2SO_4$ or a combination of $NaHSO_4$ and $Na_2SO_4$. In some instances, a filtration cake collected is characterized by loss on dry of at most 35, 40, 45, 50, 55, 60, 65 or at most 70%, where the dry substance comprises at most 50, 60, 70 or at most 80% of $NaHSO_4$, $Na_2SO_4$, or a combination of $NaHSO_4$ and $Na_2SO_4$. The solid can optionally comprise lower amounts of other metal salts of bicarbonate and/or carbonate, depending on the original composition of the black liquor. The filtrate (141) can be decanted (150) to separate the light phase comprising solvent S1 from the aqueous phase (151). The solvent S1 may optionally be recycled (152) to the re-slurry tank. In some embodiments, the aqueous phase, denoted as stream 151 in FIG. 1, comprises about 2, 3, 4, 5, 6, 7, 8% wt/wt carbohydrates and up to 38% wt/wt solvent S1. In some embodiments, aqueous phase 151 comprises about 2, 3, 4, 5, 6, 7, 8% wt/wt carbohydrates and at least 5% to at most 50%, at least 15% to at most 40%, at least 25% to at most 40%, or at least 30% to at most 40% wt/wt solvent S1.

In some aspects, stream 151 can be directed to solvent recovery 260, where solvent S1 can be optionally distilled off and recycled for further use in the process (261). In some embodiments, the bottom aqueous solution (263) is suitable for anaerobic digestion 270, including suitably low toxicity and suitably high COD values, among other required aspects. In some embodiments, the aqueous solution comprises 400 ppm or less calcium and 2,000 ppm or less sulfur, and has a high COD value of at least 35,000, 40,000, 45,000, or at least 50,000. The tolerability of anaerobic digestion to sulfur may be linearly related to COD. For example, in some cases, at COD of 30,000, sulfur concentrations at most 3,000 ppm are acceptable and do not affect stability of the microbial system. However, in some cases, at COD of 50,000 the acceptable sulfur concentration is 4,500 ppm.

Detailed Embodiments of Lignin Purification

As described hereinabove, stream 121 comprising solvent S1 and extracted lignin may be fed into a desulfurization reactor (200). The pH of the solution may be adjusted to at least pH 7.5 to at most pH 8.0 by adding a base, e.g., NaOH, LiOH or KOH. In some embodiments, the pH of the solution may be adjusted to at least pH 7.1 to at most pH 9.0 by adding a base, e.g., NaOH, LiOH or KOH. At least one desulfurization catalyst may optionally be added. In some embodiments, the catalyst is selected from a group including Raney nickel, $MoS_2$, $CoS_2$, or combination thereof. The catalyst may be any other catalyst known to catalyze desulfurization of petroleum products. Solvent S2 may be added as a hydrogen donor or reducing agent. Solvent S2 may be an alcohol, including, for example, methanol, ethanol, isopropanol, 1-butanol, 2-butanol or mixtures of the same. In some embodiments, the hydrogen donor is 2-butanol, yielding 2-butanone, i.e., MEK, which is used as solvent S1 in the process. Excess MEK produced in this process may be purged and sold as a product. In some embodiments, volatile sulfur compounds are released in the reaction (205). The volatile sulfur compounds may be vented, collected for recycling of the sulfur, or both vented and collected for recycling.

In some aspects, the efficiency of the lignin desulfurization reaction 200 is improved by the use of elevated temperatures, elevated pressures, or a combination thereof. For example, the temperature of lignin desulfurization may be in the range of at least 50° C. to at most 200° C., at least 100° C. to at most 195° C., or at least 140° C. to at most 190° C. The pressure may be in the range of 1 mPa to at most 30 mPa, for example, 12 mPa to at most 26 mPa. Further, the solution may be heated for 0.5 hours to 24 hours.

In some embodiments, the catalyst is removed from the lignin and recycled for further use (212). The catalyst may be removed either chemically or physically; for example, the catalyst may be removed via filtration 210 or using any other suitable device or process. In some embodiments, the reacted solution is filtered to remove the catalyst and the catalyst is recycled for further use (212). The solution 211 of S1 comprising the de-sulfurized lignin may be refined as disclosed earlier in PCT/US2013/039585 and PCT/US2013/068824. The organic phase comprising solvent and lignin may be contacted with strong acid cation exchanger 220 to remove residual metal cations. In further aspects, the strong acid cation exchanger can be regenerated by any suitable means. To obtain high purity solid lignin, the limited-solubility solvent may be separated from lignin, e.g., by evaporation of the limited-solubility solvent (230). In some embodiments, the limited-solubility solvent is separated from lignin by mixing the solvent solution containing acidic lignin with water at an elevated temperature (e.g., from at least 50° C. to at most 80° C.). In some aspects, the water is combined with the limited-solubility solvent under a vacuum. The precipitated lignin 231 may be recovered (240), e.g., by filtration or centrifugation. Solid lignin may be dried by application of a vacuum to the solid lignin. The solid lignin may be dissolved in any suitable solvent (e.g., phenylethyl alcohol) for making lignin solutions. In some examples, the suitable solvent is an organic solvent. In some embodiments, this process results in stream 241 (or, alternatively, 221), comprising the solvent and dissolved lignin, where residual ash is 1000 ppm or less, preferably 500 ppm or less, and wherein polyvalent cations are 500 ppm or less, preferably 200 ppm or less relative to lignin (on dry basis) and residual carbohydrates are 500 ppm or less relative to lignin (on dry basis). In some embodiments, the solution is free of particulate matter.

Optionally, the desulfurization step (200) may be omitted, thus leaving covalently bound sulfur on the lignin while removing other ash elements. Omission of the desulfurization step can result in lower-purity lignin, as typically about 1.0, 1.5, 2.0, 2.5, 3.0 or 3.5% wt/wt sulfur is covalently bound to the lignin, which may be suitable for certain applications. For example, dry lignin comprising at least 1.0, 1.5, 2.0, 2.5, 3.0, 3.2, 3.5% wt/wt or more sulfur may be used as fuel to produce energy in a paper mill, where lime kiln gases are treated to recover sulfur. In some embodiments, the lignin produced comprises at least 50%, at least 60%, at least 70%, at least 80%, at least 90%, at least 95%, or at least 99% lignin (wt/wt), at most 3.5%, 3.0%, 2.0%, 1.0%, 0.5% or 0.25% wt/wt sulfur, at most 1%, 0.5% or at most 0.025% ash, polyvalent cations in an amount up to 500 ppm or less, preferably 200 ppm or less relative to lignin and residual carbohydrates in an amount up to 500 ppm or less relative to lignin, or any combination of these specified lignin, sulfur, ash, polyvalent cation, and carbohydrate levels. In some examples, the lignin produced comprises less than 1.6% sulfur (wt/wt).

In some examples, the lignin produced comprises less than 3.5%, 3.2%, 3.0%, 2.5%, 2.0%, 1.5%, 1.0%, 0.5%, or 0.25% sulfur (wt/wt); trace S1 solvent, including but not limited to less than 10000 ppm, less than 9000 ppm, less than 8000 ppm, less than 7000 ppm, less than 6000 ppm, less than 5000 ppm, less than 4000 ppm, less than 3000 ppm, less than 2000 ppm, less than 1000 ppm, less than 500 ppm, less than 100 ppm, less than 50 ppm, less than 10 ppm, or at most 10 ppm (wt/wt) S1 solvent; and black liquor residue in an amount of at most 10000 ppm, at most 9000 ppm, at most 8000 ppm, at most 7000 ppm, at most 6000 ppm, at most 5000 ppm, at most 4000 ppm, at most 3000 ppm, at most 2000 ppm, at most 1000 ppm, at most 500 ppm, at most 100 ppm, at most 50 ppm, at most 10 ppm, or less than 10 ppm (wt/wt) black liquor residue, or any combination of these specified sulfur, S1 solvent, and black liquor residue levels.

EXAMPLES

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be included within the spirit and purview of this application and scope of the appended claims. All publications, patents, and patent applications cited herein are hereby incorporated by reference in their entirety for all purposes.

Example 1

Separation of Salts and Lignin from Black Liquor

One part of weak black liquor having 20-25% dissolved solids was mixed with 1.5 parts of 85:15 MEK:water solution to result in a 55:45 ratio of MEK:water. The solution was stirred at a temperature of 50-65° C. and was sparged with $CO_2$ slowly. After 45-60 minutes, the pH was measured in the range of 7.5-7.7. The solution was stirred for at least another hour to form a precipitate, which was then filtered through Whatman 54 filter paper with suction. The filtrate was acidified further with $H_2SO_4$ to pH 2.5-3.0 and the solution stirred at 50-65° C. for a few more minutes until the pH stabilized. The solution was centrifuged and the organic phase comprising extracted lignin collected for lignin refining. The precipitated solid was collected off the filter and re-slurried by stirring in the aqueous phase. The pH was adjusted to 2.5-3.0. A second salt precipitated, which was collected by filtration. The resulting aqueous solution comprised 6,700 mg/L sulfur and 15,200 mg/L Na. This represents a more than 50% reduction is sulfur content of the aqueous phase and a more than 70% reduction in sodium content compared to the initial black liquor. The organic phase was contacted with a strong acid cation (SAC) resin in the $H^+$ form. The MEK solution was added dropwise into an aqueous bath at 80° C., causing flash evaporation of the solvent and precipitation of lignin particles in the aqueous phase. The solid was collected by filtration and dried. This lignin product comprised 2.5% sulfur, 60 mg/kg Ca, no detectable Fe, K, Mg or Na. The ICP results of samples collected in the process are summarized in Table 1.

TABLE 1

ICP analysis of samples collected at steps of salt and lignin separation from black liquor (n.d. means not detected).

| Sample | Ref# | S | Ca | K | Na |
|---|---|---|---|---|---|
| | | \multicolumn{4}{c}{mg/L} | | | |
| Black Liquor | 18900 | 14000 | n.d. | 4260 | 51000 |
| Black Liquor and MEK-organic phase | 18901O | 125 | n.d. | n.d. | n.d. |

TABLE 1-continued

ICP analysis of samples collected at steps of salt and lignin separation from black liquor (n.d. means not detected).

| Sample | Ref# | S | Ca | K | Na |
|---|---|---|---|---|---|
| Black Liquor and MEK-aqueous phase | 18901A | 13400 | n.d. | 4150 | 47000 |
| Filtrate after salts filtered out - organic phase | 18903 | 3460 | n.d. | 3100 | 24600 |
| Filtrate after salts filtered out - aqueous phase | 18904 | 6700 | n.d. | n.d. | 15200 |
| 10.3 grams filter cake oven dried and slurried in 40 grams water | 18902 | 5400 | n.d. | 4900 | 24100 |
| Extracted & ion exchanged Lignin | 18905 | 25000 | 60 | n.d. | n.d. |

Example 2

Refining of Lignin from Black Liquor

Lignin refined according to Example 1 (yielding ~2 grams), having 2.7% residual sulfur was slurried in water (ca. 20 ml). An aqueous solution of NaOH (5%) was added to the mixture to reach pH 12.5-13.0 and to solubilize the precipitated lignin. Then, 60 ml of 80:20 MEK:water (vol/vol) mixture was added. The pH of the mixture was adjusted to 2.0-2.5 via addition of $H_2SO_4$. The organic phase was separated by decantation. MEK solution (20 ml) comprising ~6% lignin was desulfurized via addition of molybdenum sulfide (~1 g) as a catalyst and methanol (10 ml) as a hydrogen donor. The mixture was further stirred at 175° C. for 2 hours under nitrogen pressure (225-325 psi reaction pressure). Each reaction yielded about 30 ml of the crude reaction mixture. The reactions were combined and methanol distilled off. The solution was contacted with SAC, and lignin collected by flash vaporization and dried.

Example 3

Characterization of Refined Lignin

Lignin was separated from black liquor according to Examples 1 and 2. The organic phase comprising lignin was contacted with SAC resin in the $H^+$ form. Solid lignin was obtained by flash evaporation of the solvent, and the resulting solid lignin was filtered and dried.

Elemental Analysis: The purified lignin sample derived from black liquor was analyzed by elemental analysis for C, H, N, O and S. The results of the characterization are summarized in Table 2 (column labeled "Refined Black Liquor"), and compared to lignin prepared by Virdia CASE™ method and literature values for Kraft softwood (SW) lignin.

TABLE 2

Elemental analysis of lignin compositions

| | | | % | | | |
|---|---|---|---|---|---|---|
| Elements | Refined Black Liquor | CASE™ Eucalyptus | CASE™ Pine | CASE™ Bagasse | Kraft SW | Lignosulfonate |
| C | 64.7 | 62.1 | 67.1 | 66.2 | 64.3 | 42.0 |
| H | 5.90 | 5.91 | 6.68 | 6.71 | 6.0 | 4.6 |
| N | N.D. | 0.12 | 0.12 | 0.35 | N.D. | 0 |
| O | 22.7 | 27.5 | 23.4 | 23.6 | 27.9 | 47.1 |
| S | 1.52 | N.D. | N.D. | N.D. | 1.8 | 6.3 |
| Formula | $C_9H_{9.85}O_{2.37}$ | $C_9H_{10.28}O_{2.99}$ | $C_9H_{10.75}O_{2.35}$ | $C_9H_{10.94}O_{2.40}$ | $C_9H_{10.01}O_{3.9}$ | $C_9H_{11.83}O_{4.81}$ |

TABLE 2-continued

Elemental analysis of lignin compositions

%

| Elements | Refined Black Liquor | CASE™ Eucalyptus | CASE™ Pine | CASE™ Bagasse | Kraft SW | Ligno-sulfonate |
|---|---|---|---|---|---|---|
| O/C | 0.26 | 0.33 | 0.26 | 0.27 | 0.35 | 0.53 |
| H/C | 1.09 | 1.14 | 1.19 | 1.22 | 1.1 | 1.31 |

$^{13}$C NMR: Lignin was characterized by solid state $^{13}$C NMR. The results are summarized in Table 3.

TABLE 3

$^{13}$C NMR of Lignin compositions
(s = syringil, g = guiacyl, h = hydroxyl cumaril).

| | Refined Black Liquor | ASE Eucalyptus Lignin | ASE Pine Lignin | ASE Bagasse Lignin | Residual Kraft Softwood |
|---|---|---|---|---|---|
| Degree of condensation | 0.8 | 0.6 | 0.8 | 0.4 | 1 |
| Methoxyl content (#/aryl group) | 0.8 | 1.3 | 0.8 | 0.9 | 0.8 |
| Aliphatic linkages (β-O-4') (#/aryl group) | 0.2 | 0.5 | 0.1 | 0.2 | 0.3 |
| Aromatic C—O (#/aryl group) | 1.9 | 2.0 | 1.9 | 1.7 | 2.1 |
| Aromatic C—C (#/aryl group) | 2.0 | 2.1 | 2.0 | 2.2 | 1.9 |
| Aromatic C—H (#/aryl group) | 2.2 | 1.9 | 2.2 | 2.1 | 2.0 |
| S:G | — | 1.1 | — | 0.7 | — |
| h:g:s | | | | 28:42:30 | |

What is claimed is:

1. A process for separating lignin from black liquor, the process comprising:
   (i) contacting the black liquor with a limited-solubility solvent, thereby forming a mixture;
   (ii) neutralizing the mixture by addition of $CO_2$;
   (iii) filtering the mixture, thereby generating a filtrate and a filtration cake;
   (iv) acidifying the filtrate;
   (v) separating the filtrate into an organic phase and an aqueous phase;
   (vi) removing metal cations from the organic phase; and
   (vii) recovering lignin from the organic phase.

2. The process of claim 1, wherein the limited-solubility solvent comprises a 4-to 8-carbon ketone.

3. The process of claim 2, wherein the limited-solubility solvent is methyethyl ketone.

4. The process of claim 1, wherein the contacting the black liquor with the limited-solubility solvent induces precipitation of a salt.

5. The process of claim 4, wherein the salt comprises a carbonate, bicarbonate, sulfate, or bisulfate ion.

6. The process of claim 1, wherein the mixture is maintained at a temperature of at least 30° C. to at most 90° C. during the addition of $CO_2$.

7. The process of claim 1, further comprising halting the addition of $CO_2$ once the mixture has a pH of at least 7.1 to at most 9.5.

8. The process of claim 1, wherein the acidifying of the filtrate is accomplished by addition of a mineral acid.

9. The process of claim 1, wherein the recovering lignin from the organic phase comprises evaporating the organic phase, thereby forming a solid lignin.

10. The process of claim 1, wherein the recovering lignin from the organic phase comprises contacting the organic phase with water at an elevated temperature, thereby forming a lignin precipitate.

11. The process of claim 10, further comprising filtering the lignin precipitate, thereby collecting a solid lignin.

12. The process of claim 11, further comprising dissolving the solid lignin in an organic solvent.

13. The process of claim 12, further comprising subjecting the lignin solution to desulfurization reaction conditions.

14. The process of claim 13, wherein the desulfurization reaction conditions comprise a desulfurization catalyst.

15. The process of claim 14, wherein the desulfurization catalyst is selected from Raney nickel, $MoS_2$, $CoS_2$, or a combination thereof.

16. The process of claim 13, wherein the desulfurization reaction conditions comprise a hydrogen donor.

17. The process of claim 16, wherein the hydrogen donor is an alcohol.

18. The process of claim 17, wherein the hydrogen donor is 2-butanol.

19. The process of claim 1, further comprising subjecting lignin in the organic phase to desulfurization reaction conditions.

20. The process of claim 19, wherein the desulfurization reaction conditions comprise a desulfurization catalyst.

21. The process of-claim 1, further comprising contacting the filtration cake with the aqueous phase of the acidified filtrate, thereby forming a slurry.

22. The process of claim 21, further comprising separating an aqueous solution suitable for anaerobic digestion from the slurry.

23. The process of claim 22, further comprising anaerobically digesting the aqueous solution suitable for anaerobic digestion to produce methane.

24. The process of claim 1, wherein the removing metal cations from the organic phase comprises contacting the organic phase with a strong acid cation exchange resin.

* * * * *